(12) United States Patent
Abbot et al.

(10) Patent No.: US 8,168,792 B2
(45) Date of Patent: May 1, 2012

(54) HETEROCYCLIC ANTIVIRAL COMPOUNDS

(75) Inventors: Sarah C. Abbot, Erie, PA (US); Alfred Sui-Ting Lui, Sunnyvale, CA (US); Jim Li, San Francisco, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 166 days.

(21) Appl. No.: 12/718,207

(22) Filed: Mar. 5, 2010

(65) Prior Publication Data
US 2010/0226879 A1  Sep. 9, 2010

Related U.S. Application Data

(60) Provisional application No. 61/158,207, filed on Mar. 6, 2009.

(51) Int. Cl.
*C07D 215/00* (2006.01)
(52) U.S. Cl. ...................................................... 546/157
(58) Field of Classification Search .................. 546/157
See application file for complete search history.

(56) References Cited

U.S. PATENT DOCUMENTS

2004/0087577 A1   5/2004   Pratt et al.

FOREIGN PATENT DOCUMENTS

| WO | WO00/09543 A2 | 2/2000 |
|---|---|---|
| WO | WO01/85172 A1 | 11/2001 |
| WO | 2008082424 A1 | 7/2008 |
| WO | WO2009/039135 A1 | 3/2009 |
| WO | WO2010/111436 A2 | 9/2010 |
| WO | WO2010/111437 A1 | 9/2010 |

OTHER PUBLICATIONS

Bosse et al., Bioorg. Med. Chem. Lett. 2008, 18, 568-570.*
Venkatesh et al., J. Pharm. Sci. 89, 145-54 (2000).*
Dorwald F. A. (Side Reactions in Organic Synthesis, 2005, Wiley: VCH, Weinheim p. IX of Preface p. 1-15).*

* cited by examiner

Primary Examiner — Nizal Chandrakumar
(74) Attorney, Agent, or Firm — Brian L. Buckwalter

(57) ABSTRACT

Compounds having the formula A-R wherein A is a heteroaryl and R is Ia, Ib or Ic and wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as are as defined herein are Hepatitis C virus NS5b polymerase inhibitors. Also disclosed are compositions and methods for treating an HCV infection and inhibiting HCV replication.
R is

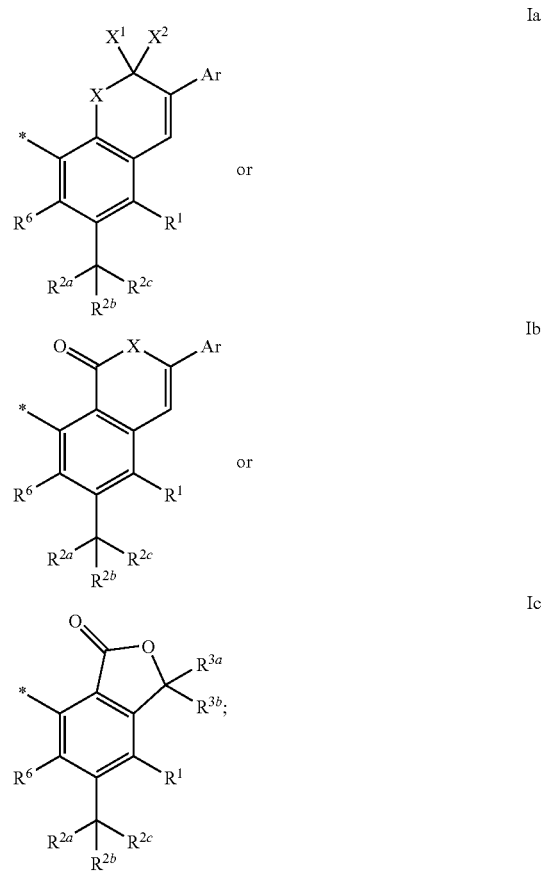

14 Claims, No Drawings

HETEROCYCLIC ANTIVIRAL COMPOUNDS

CROSS-REFERENCE TO PRIOR APPLICATIONS

This application claims the benefit of priority to U.S. Ser. No. 61/158,207 filed Mar. 6, 2009 which is hereby incorporated by reference in their entirety.

FIELD OF THE INVENTION

The present invention provides non-nucleoside compounds of formula A-R, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American, October:* 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8):1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose significant clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase, NS5A and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. Cellular kinases often convert the nucleoside to the triphosphate which imparts additional structural limitations on the nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22): 6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Examples of the interferons include, but are not limited to pegylated rIFN-α 2b, pegylated rIFN-α 2a, rIFN-α 2b, rIFN-α 2a, consensus IFN α (infergen), Reaferon, INTERMAX ALPHA, r-IFN-beta, INFERGEN and ACTIMMUNE, IFN-omega with DUROS, ALBUFERON, LOCTERON, ZALBIN, REBIF, oral interferon α, IFNα-2b XL, AVI-005, PEG-Infergen, and pegylated IFN-β.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 and BMS-605339 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula A-R, or a pharmaceutically acceptable salt thereof, wherein:

A is a heteroaryl radical selected from the group consisting of 2-oxo-1,2-dihydro-pyridin-3-yl, 3-oxo-3,4-dihydro-pyrazin-2-yl, 3-oxo-2,3-dihydro-pyridazin-4-yl, 2-oxo-1,2-dihydro-pyrimidin-4-one-5-yl and 6-oxo-1,6-dihydro-[1,2,4]triazin-5-yl said heteroaryl being optionally substituted by halogen, $C_{1-6}$ alkyl, $C_{1-3}$ haloalkyl or $C_{1-6}$ alkoxy.

R is Ia, Ib or Ic;

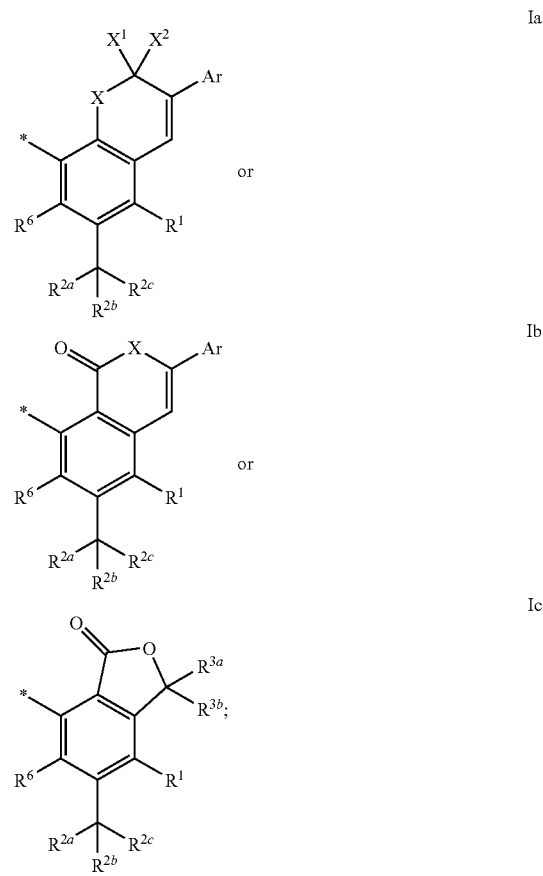

X is $NR^4$ or O.

If X is O, $X^1$ and $X^2$ together are oxo, or one of $X^1$ and $X^2$ is OH or $C_{1-3}$ alkoxy and the other of $X^1$ and $X^2$ is hydrogen; or, if X is $NR^4$, $X^1$ and $X^2$ together are oxo.

$R^{3a}$ is hydrogen and $R^{3b}$ is $CH_2Ar$ or $R^{3a}$ and $R^{3b}$ together are =CHAr.

Ar is phenyl, pyridinyl, pyrimidinyl, pyrazinyl or pyridazinyl optionally independently substituted with one to three substitutents selected from the group consisting of (a) hydroxy, (b) $C_{1-6}$ alkoxy, (c) $C_{1-6}$ alkyl, (d) $C_{1-6}$ hydroxyalkyl, (f) halogen, (h) cyano, (i) $CO_2R^5$, (j) $CONR^cR^d$, (k)

$C_{1-3}$ acylamino, (l) $(CH_2)_nNR^aR^b$, (m) $(CH_2)_nCONR^cR^d$, (n) $(CH_2)_nSO_2NR^cR^d$, (o) $(CH_2)_nSO_2R^5$ and (p) $O(CH_2)_nCONR^cR^d$.

$R^a$ and $R^b$ are independently in each occurrence (a) hydrogen, (b) $C_{1-6}$ alkyl, (c) $C_{1-6}$ acyl, (d) $C_{1-6}$ alkylsulfonyl, (e) $C_{1-6}$ haloalkylsulfonyl, (f) $C_{3-7}$ cycloalkylsulfonyl, (g) $C_{3-7}$ cycloalkyl-$C_{1-3}$ alkyl-sulfonyl or (h) $C_{1-6}$ alkoxy-$C_{1-6}$ alkyl-sulfonyl, (i) $SO_2(CH_2)_nNR^cR^d$, (j) carbamoyl, (k) $C_{1-3}$ alkylcarbamoyl, (l) $C_{1-3}$ dialkylcarbamoyl or (m) benzoyl said benzoyl optionally independently substituted with one or two groups selected from the group consisting of amino, halogen, $C_{1-6}$ alkyl or $C_{1-3}$ alkylsulfonylamino.

$R^c$ and $R^d$ are independently in hydrogen, $C_{1-6}$ alkyl, $C_{1-6}$ acyl, or together with the nitrogen atom to which they are attached are a cyclic amine.

$R^1$ is hydrogen, $C_{1-6}$ alkyloxy or $C_{1-6}$ haloalkyloxy or $R^1$ and $R^{2a}$ together are $CH_2$—O and together with atoms to which they are attached form a 2,3-dihydrobenzofuran.

$R^6$ is hydrogen or $R^6$ and $R^{2a}$ together are $CH_2$—O and together with atoms to which they are attached form a 2,3-dihydrobenzofuran.

$R^4$ is hydrogen or $C_{1-6}$ alkyl.

$R^5$ is hydrogen, $C_{1-6}$ alkyl, $C_{1-6}$ haloalkyl, $C_{1-3}$ alkoxy-$C_{1-3}$ alkyl or optionally substituted benzyl.

$R^{2a}$, $R^{2b}$ and $R^{2c}$ (i) when taken independently are selected independently from $C_{1-3}$ alkyl, $C_{1-2}$ alkoxy or $C_{1-2}$ fluoroalkyl or (ii) when taken together, $R^{2a}$ and $R^{2b}$ together are $C_{2-4}$ methylene and $R^{2c}$ is $C_{1-3}$ alkyl, $C_{1-2}$ alkoxy, halogen or $C_{1-2}$ fluoroalkyl; or (iii) either $R^1$ or $R^6$ and $R^{2a}$ together are $CH_2$—O and together with atoms to which they are attached form a 2,3-dihydro-benzofuran and $R^{2b}$ and $R^{2c}$ are $C_{1-3}$ alkyl.

n is independently in each occurrence an integer from zero to three.

The present invention further comprises pharmaceutically acceptable salt of compounds of formula I as herein described.

The present invention also provides a method for treating a disease a Hepatitis C Virus (HCV) virus infection by administering a therapeutically effective quantity of a compound according to formula A-R to a patient in need thereof. The compound can be administered alone or co-administered with other antiviral compounds or immunomodulators.

The present invention also provides a method for inhibiting replication of HCV in a cell by administering a compound according to formula A-R in an amount effective to inhibit HCV.

The present invention further provides a pharmaceutical composition comprising a compound according to formula A-R and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all embodiments described below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

The symbols "*" at the end of a bond or "------" drawn through a bond each refer to the point of attachment of a functional group or other chemical moiety to the rest of the molecule of which it is a part. Thus, for example:

$MeC(=O)OR^4$ wherein $R^4=$

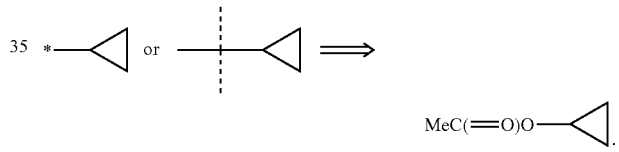

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula A-R exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula A-R may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae A-R and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, α-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxillary) to produce diastereomers which can be separated by chromatography or by fractional crystallization after which time the chiral auxiliary is chemically removed to afford the pure enantiomers.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to formula I wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above. In all other embodiments provided below, substituents which can be present in each embodiment and which are not explicitly limited retain the broadest definition provided in the Summary of the Invention.

In an embodiment of the present invention there is provided a compound according to formula I wherein A is 2-oxo-1,2-dihydro-pyridin-3-yl, R is Ia, X is $NR^4$ or O, $X^1$ and $X^2$ together are oxo, Ar is optionally substituted phenyl and $R^{2a}$, $R^{2b}$ and $R^{2c}$ each are methyl.

In another embodiment of the present invention there is provided a compound according to formula I wherein A is 2-oxo-1,2-dihydro-pyridin-3-yl, R is Ia, X is $NR^4$ or O, $X^1$ and $X^2$ together are oxo, Ar is optionally substituted phenyl and $R^1$ and $R^{2a}$ together are $CH_2$—O and together with atoms to which they are attached form a 2,3-dihydro-benzofuran and $R^{2b}$ and $R^{2c}$ are $C_{1-3}$ alkyl.

In yet another embodiment of the present invention there is provided a compound according to formula I wherein A is 2-oxo-1,2-dihydro-pyridin-3-yl, R is Ia, X is $NR^4$ or O, $X^1$ and $X^2$ together are oxo, Ar is optionally substituted phenyl and $R^6$ and $R^{2a}$ together are $CH_2$—O and together with atoms to which they are attached form a 2,3-dihydro-benzofuran and $R^{2b}$ and $R^{2c}$ are $C_{1-3}$ alkyl.

In still another embodiment of the present invention there is provided a compound according to formula I wherein A is 2-oxo-1,2-dihydro-pyridin-3-yl, R is Ia, X is $NR^4$ or O, $X^1$ and $X^2$ together are oxo, Ar is optionally substituted phenyl and $R^{2a}$ and $R^{2b}$ taken together are ethylene and $R^{2c}$ is $C_{1-3}$ alkyl, halogen or $C_{1-2}$ fluoroalkyl;

In another embodiment of the present invention there is provided a compound according to formula I wherein A is 2-oxo-1,2-dihydro-pyridin-3-yl, R is Ia, X is $NR^4$ or O, $X^1$ and $X^2$ together are oxo, Ar is phenyl substituted at least by $(CH_2)_nNR^aR^b$ wherein $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen, n is zero and $R^{2a}$, $R^{2b}$ and $R^{2c}$ each are methyl.

In another embodiment of the present invention there is provided a compound according to formula I wherein A is 3-oxo-3,4-dihydro-pyrazin-2-yl, R is Ia, X is $NR^4$ or O, $X^1$ and $X^2$ together are oxo, Ar is phenyl substituted at least by $(CH_2)_nNR^aR^b$ wherein $R^a$ is $C_{1-6}$ alkylsulfonyl, $R^b$ is hydrogen and n is zero, $R^{2a}$, $R^{2b}$ and $R^{2c}$ each are methyl.

In another embodiment of the present invention there is provided a compound according to formula I wherein A is 3-oxo-2,3-dihydro-pyridazin-4-yl, R is Ia, X is $NR^4$ or O, $X^1$ and $X^2$ together are oxo, Ar is phenyl substituted at least by $(CH_2)_nNR^aR^b$ wherein $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen, n is zero and $R^{2a}$, $R^{2b}$ and $R^{2c}$ each are methyl.

In another embodiment of the present invention there is provided a compound according to formula I wherein A is 2-oxo-1,2-dihydro-pyridin-3-yl and R is Ib.

In another embodiment of the present invention there is provided a compound according to formula I wherein A is 2-oxo-1,2-dihydro-pyridin-3-yl, R is Ib, Ar is optionally substituted phenyl and $R^{2a}$, $R^{2b}$ and $R^{2c}$ each are methyl.

In another embodiment of the present invention there is provided a compound according to formula I wherein A is 2-oxo-1,2-dihydro-pyridin-3-yl, R is Ib, Ar is phenyl substituted at least by $(CH_2)_nNR^aR^b$, $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen, n is zero and $R^{2a}$, $R^{2b}$, and $R^{2c}$ each are methyl.

In another embodiment of the present invention there is provided a compound according to formula I wherein A is 2-oxo-1,2-dihydro-pyridin-3-yl and R is Ic.

In another embodiment of the present invention there is provided a compound according to formula I wherein A is 2-oxo-1,2-dihydro-pyridin-3-yl and R is Ic, $R^{3a}$ is hydrogen and $R^{3b}$ is $CH_2Ar$, Ar is optionally substituted phenyl and $R^{2a}$, $R^{2b}$, $R^{2c}$ each are methyl.

In another embodiment of the present invention there is provided a compound according to formula I wherein A is 2-oxo-1,2-dihydro-pyridin-3-yl and R is Ic, $R^{3a}$ is hydrogen and $R^{3b}$ is $CH_2Ar$, Ar is optionally substituted phenyl, $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen, n is zero and $R^{2a}$, $R^{2b}$ and $R^{2c}$ each are methyl.

In another embodiment of the present invention there is provided a compound according to formula I wherein A is 2-oxo-1,2-dihydro-pyridin-3-yl and R is Ic, $R^{3a}$ and $R^{3b}$ together are =CHAr, Ar is optionally substituted phenyl and $R^{2a}$, $R^{2b}$ and $R^{2c}$ are methyl.

In another embodiment of the present invention there is provided a compound according to formula I wherein A is 2-oxo-1,2-dihydro-pyridin-3-yl and R is Ic, $R^{3a}$ and $R^{3b}$ together are =CHAr, Ar is optionally substituted phenyl and $R^{2a}$, $R^{2b}$ and $R^{2c}$ are methyl.

In another embodiment the is provided a compound according to formula I selected from the compounds I-1 to I-18 in TABLE I.

In another embodiment of the present invention there is provide a method of treating a HCV infection in a patient in need thereof comprising administering a therapeutically effective amount of a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined hereinabove.

In another embodiment of the present invention there is provide a method of treating a HCV infection in a patient in need thereof comprising co-administering a therapeutically effective amount of a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above and at least one immune system modulator and/or at least one antiviral agent that inhibits replication of HCV.

In another embodiment of the present invention there is provide a method of treating a disease caused by HCV in a patient in need thereof comprising co-administering a therapeutically effective amount of a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above and at least one immune system modulator selected from interferon, interleukin, tumor necrosis factor or colony stimulating factor.

In another embodiment of the present invention there is provide a method of treating a HCV infection in a patient in need thereof comprising co-administering a therapeutically effective amount of a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above and an interferon or chemically derivatized interferon.

In another embodiment of the present invention there is provide a method of treating a HCV infection in a patient in need thereof comprising co-administering a therapeutically effective amount of a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In another embodiment of the present invention there is provided a method for inhibiting viral replication in a cell by delivering a therapeutically effective amount of a compound of the formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above admixed with at least one pharmaceutically acceptable carrier, diluent or excipient.

In another embodiment of the present invention there is provided a composition comprising a compound according to formula A-R wherein A, R, $R^1$, $R^{2a}$, $R^{2b}$, $R^{2c}$, $R^{3a}$, $R^{3b}$, $R^4$, $R^5$, $R^6$, $R^a$, $R^b$, $R^c$, $R^d$, X, $X^1$, $X^2$ and n are as defined herein above admixed with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, tert-butyl, tert-butyl, neopentyl, hexyl, and octyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH$(i-Pr)$CH_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. $C_{2-4}$ methylene refers to $(CH_2)_{2-4}$. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 1 2-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "hydroxyalkoxy" and "alkoxyalkoxyl" as used herein denotes alkoxy radical as herein defined wherein one to three hydrogen atoms on different carbon atoms is/are replaced by hydroxyl or alkoxy groups respectively. A C1-3 alkoxy-C1-6 alkoxy moiety refers to a C1-6 alkoxy substituent in which 1 to 3 hydrogen atoms are replaced by a C1-3 alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "cyano" as used herein refers to a carbon linked to a nitrogen by a triple bond, i.e., —C≡N. The term "nitro" as used herein refers to a group —$NO_2$. The term "carboxy" as used herein refers to a group —$CO_2H$.

The term oxo refers to a doubly bonded oxygen (=O), i.e. a carbonyl group.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl or "alkanoyl" refers to a group —C(=O)R contain 1 to 6 carbon atoms. The $C_1$ acyl group is the formyl group wherein R=H and a C6 acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "acylamino" as used herein denotes a group of formula —NHC(=O)R wherein R is hydrogen or lower alkyl as defined herein. $C_{1-6}$ acyl-amino refers to an acylamino group wherein the C(=O)R moiety contains a total of 6 carbon atoms.

The term "cyclic amine" as used herein refers to a saturated carbon ring, containing from 3 to 6 carbon atoms as defined above, and wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazo line, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by $C_{1-6}$ alkyl, $C_{1-6}$ acyl, $C_{1-6}$ alkylsulfonyl.

The terms "alkylsulfonyl" and "arylsulfonyl" as used herein denotes a group of formula —S(=O)$_2$R wherein R is alkyl or aryl respectively and alkyl and aryl are as defined herein. The term $C_{1-3}$ alkylsulfonylamino as used herein refers to a group $RSO_2NH$— wherein R is a $C_{1-3}$ alkyl group as defined herein. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, S(=O)$_2$R wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively.

The terms "alkylsulfonylamino" and "arylsulfonylamino" as used herein denotes a group of formula —NR'S(=O)$_2$R wherein R is alkyl or aryl respectively, R' is hydrogen or $C_{1-3}$ alkyl, and alkyl and aryl are as defined herein.

The term "sulfamoyl" as used herein refers to the radical —S(O)$_2NH_2$. The terms "N-alkylsulfamoyl" and "N,N-dialkylsulfamoyl" as used herein refers to the radical —S(O)$_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propyl-methylaminosulfonyl.

The term "carbamoyl" as used herein means the radical —CONH$_2$. The prefix "N-alkylcabamoyl" and "N,N-dialkylcarbamoyl" means a radical CONHR' or CONR'R" respectively wherein the R' and R" groups are independently alkyl as defined herein. The prefix N-arylcabamoyl" denotes the radical CONHR' wherein R' is an aryl radical as defined herein.

The term "benzyl" as used herein refers to a C$_6$H$_5$CH$_2$ radical wherein the phenyl ring which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylamino sulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated.

The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered non-fused heteroaromatic ring with two nitrogen atoms disposed in a 1,3, a 1,4 and a 1,2 relationship respectively. The respective radical names are in parentheses.

The terms (i) 3-oxo-3,4-dihydro-pyrazin-2-yl, (ii) 3-oxo-2,3-dihydro-pyridazin-4-yl or (iii) 2-oxo-1,2-dihydro-pyrimidin-4-one-5-yl, (iv) 2-oxo-1,2-dihydro-pyridin-3-yl and (v) 6-oxo-1,6-dihydro-[1,2,4]triazin-5-yl refer to the following moieties:

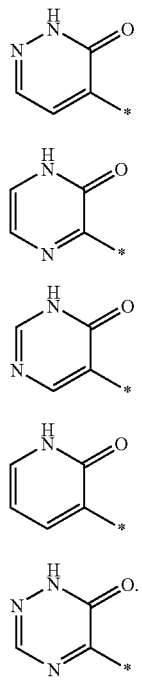

The phrase "substituted at least by (CH$_2$)$_n$NR$^c$R$^{d}$" in reference to Ar simply indicates the ring is substituted by (CH$_2$)$_n$NR$^c$R$^d$ but does not preclude additional optional substitutions within the scope of the claim are permitted at unsubstituted carbon atoms.

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and anti-infective compounds. Such combination therapy may also comprise providing a compound of the invention either concurrently or sequentially with other medicinal agents or potentiators, such as ribavirin and related compounds, amantadine and related compounds, various interferons such as, for example, interferon-α, interferon-β, interferon γ and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950

(telaprevir, Vertex), BILN-2065 (Boehringer-Ingelheim, BMS-605339 (Bristol Myers Squibb), and ITMN-191 (Intermune).

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-$BuMe_2Si$ (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in TABLE I. These examples and preparations which follow are provided to enable those skilled in the art to more clearly understand and to practice the present invention. They should not be considered as limiting the scope of the invention, but merely as being illustrative and representative thereof. Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted as a Markush structure with generalized substituents; however, one skilled in the art will immediately appreciate that the nature of the R groups as defined in the claims can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof

TABLE I

| Cpd. No. | STRUCTURE | ms | mp | IC$_{50}$ (μM) HCV Pol[1] |
|---|---|---|---|---|
| I-1 | 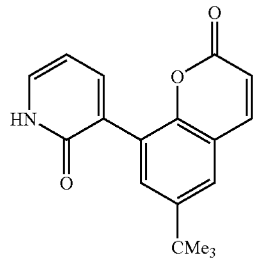 | 296 | >300 | 1.53 |
| I-2 | 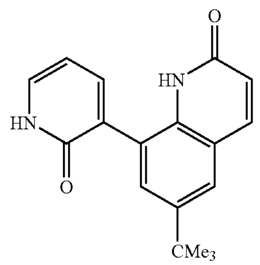 | 295 | >300 | 0.332 |
| I-3 | 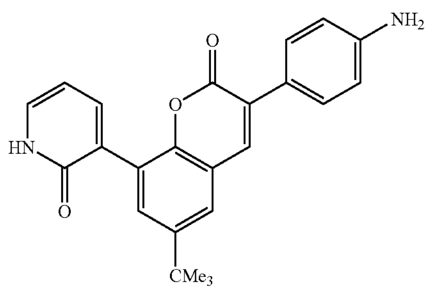 | 387 | >300 | 0.034 |
| I-4 | 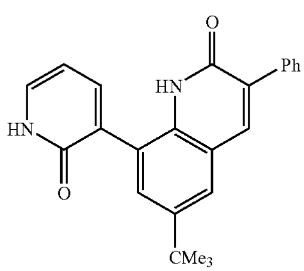 | 371 | 200-202 | 0.091 |
| I-5 | 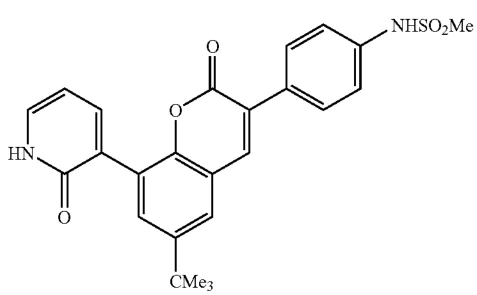 | 465 | 225.0-227.0 | 0.005 |

TABLE I-continued

| Cpd. No. | STRUCTURE | ms | mp | IC$_{50}$ (μM) HCV Pol[1] |
|---|---|---|---|---|
| I-6 | 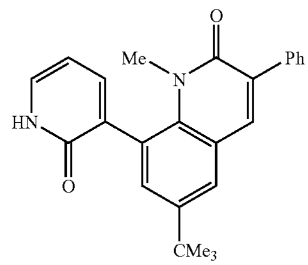 | 385 | 290.0-292.0 | 0.456 |
| I-7 | 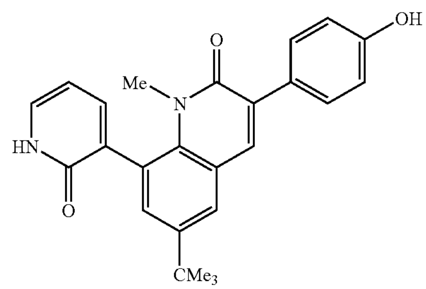 | 401 | >300 | 0.9 |
| I-8 | 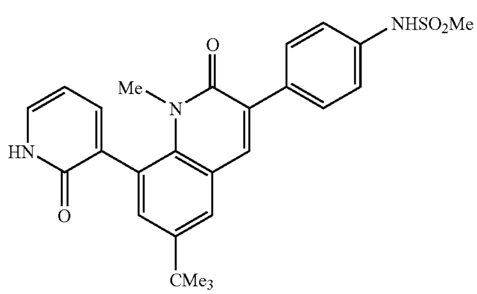 | 478 | >300 | 0.006 |
| I-9 | 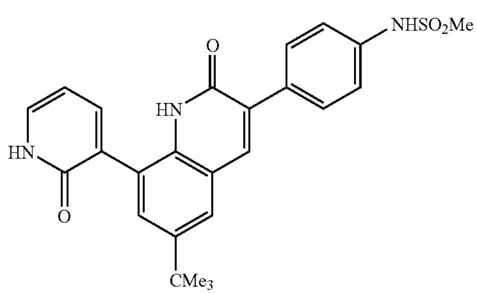 | 464 | >300 | 0.005 |
| I-10 | 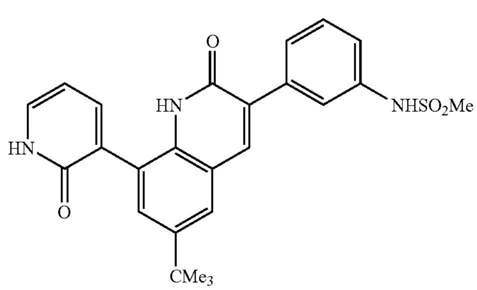 | 464 | 233.0-235.0 | 0.531 |

TABLE I-continued

| Cpd. No. | STRUCTURE | ms | mp | IC$_{50}$ (μM) HCV Pol[1] |
|---|---|---|---|---|
| I-11 | 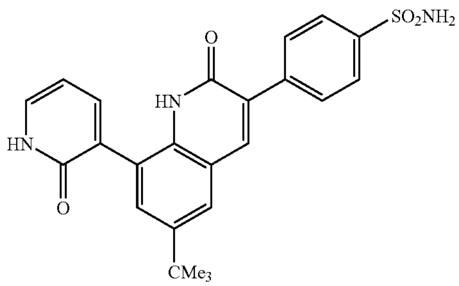 | 450 | 250.0-252.0 | 0.046 |
| I-12 | 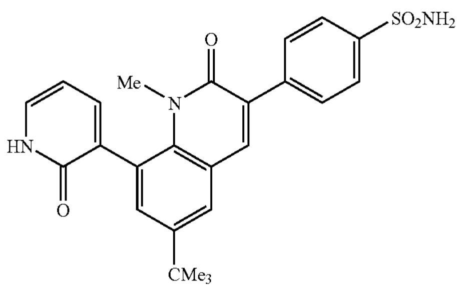 | 464 | >300 | 2.37 |
| I-13 | 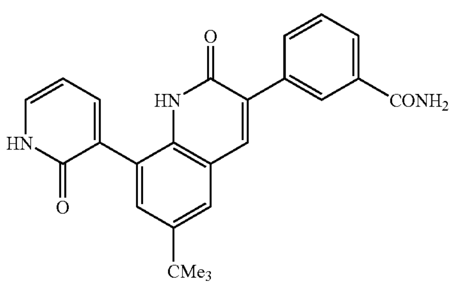 | 414 | 255.0-257.0 | 0.036 |
| I-14 | 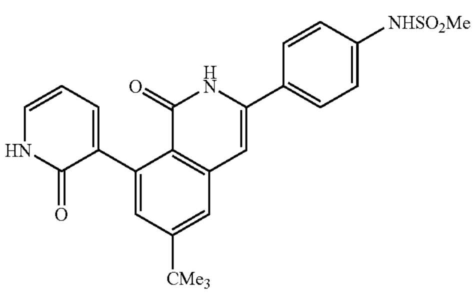 | 464 | >300 | 0.016 |
| I-15 | 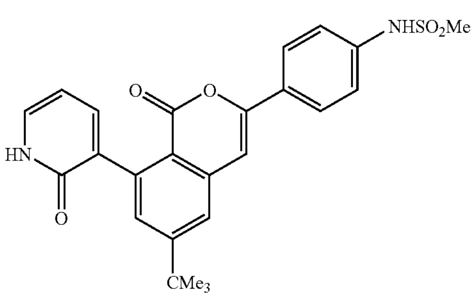 | 465 | | 0.008 |

TABLE I-continued

| Cpd. No. | STRUCTURE | ms | mp | IC$_{50}$ (μM) HCV Pol[1] |
|---|---|---|---|---|
| I-16 | 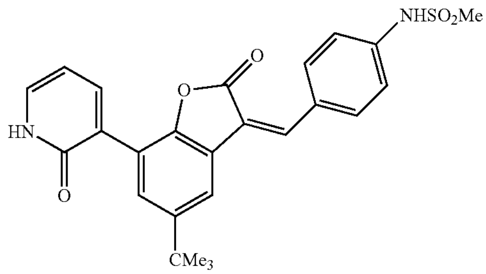 | 465 | | 0.033 |
| I-17 | 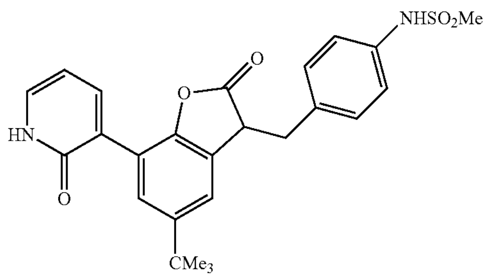 | 467 | 180.0-182.0 | 0.027 |
| I-18 | 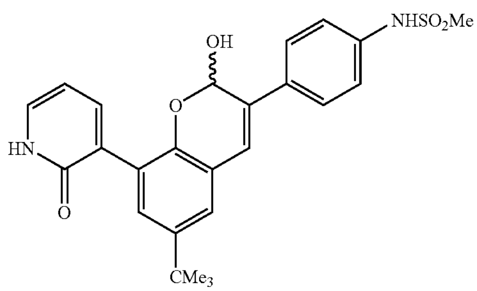 | 469 | 228.0-230.0 | 0.007 |

[1]HCV polymerase assay in Example 11

Compounds in following schemes are frequently depicted with generalized substituents to exemplify the general nature of the methodology. One skilled in the art will immediately appreciate that the nature of the R groups can varied to afford the various compounds contemplated in this invention. Moreover, the reaction conditions are exemplary and alternative conditions are well known which can be substituted for the conditions described herein. The SCHEMES which follow exemplify general routes which can be used to prepare compounds encompassed by the present invention and are not limiting. Details of the preparation of specific compounds can be found in the examples which follow. The reaction sequences in the following examples are not meant to limit the scope of the invention as set forth in the claims.

1H-quinolin-2-ones and chromen-2-ones can be prepared by introducing a propionic acid moiety adjacent to a suitably substituted phenol or aniline. One approach is exemplified with the preparation of 6-alkyl-8-(2-oxo-1,2-dihydro-pyridin-3-yl)-3-phenyl-1H-quinolin-2-one compounds utilizing a Heck reaction to introduce a three carbon fragment, ethyl acrylate, onto a 4-alkyl-2,6-dibromoaniline such as 2,6-dibromo-4-tert-butylaniline (30, CASRN 10546-67-5) to afford 32.

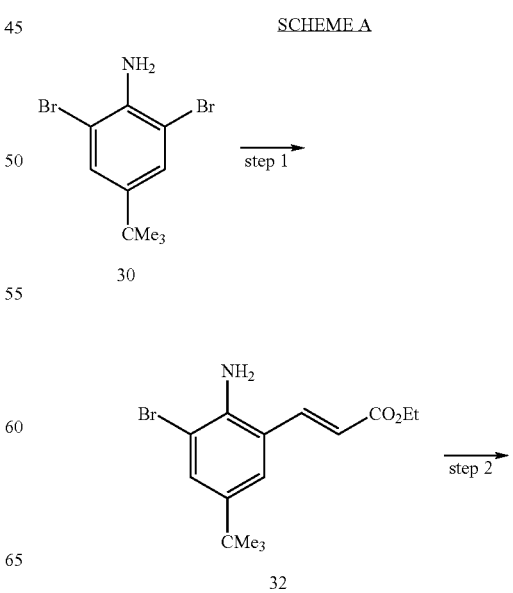

SCHEME A

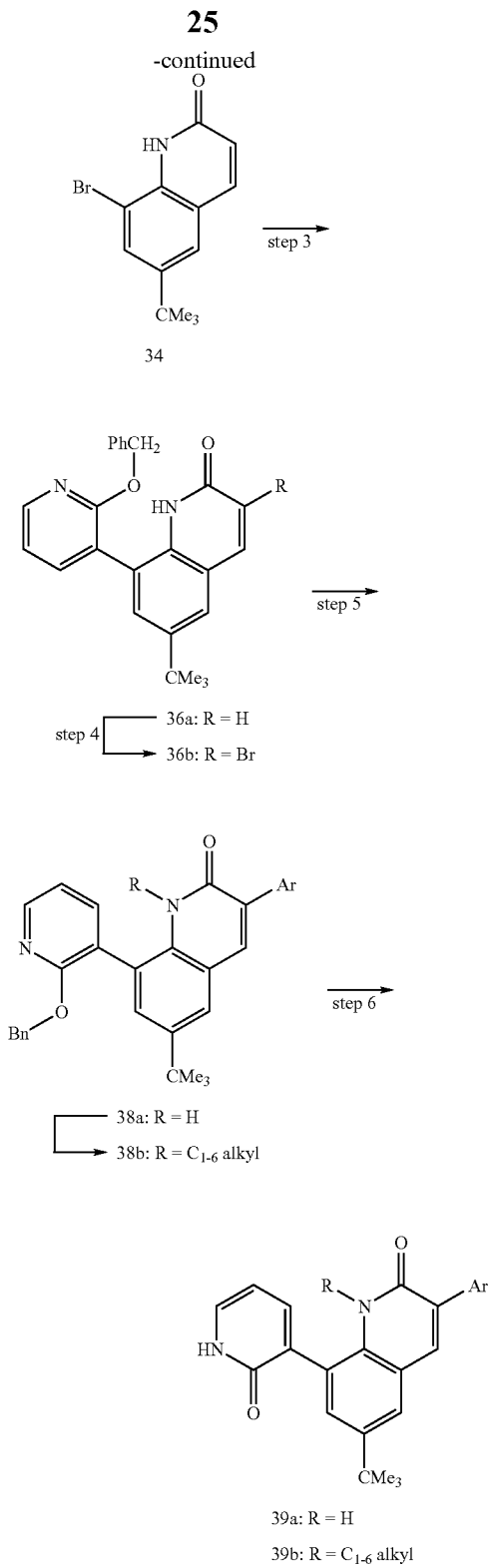

36a: R = H
36b: R = Br

38a: R = H
38b: R = C<sub>1-6</sub> alkyl

39a: R = H
39b: R = C<sub>1-6</sub> alkyl

The Heck (or Mizoroki-Heck) reaction is the palladium-catalyzed coupling of an aryl, alkenyl, alkynyl or benzyl halide or triflate with an alkene, styrene, acrylate ester, acrylonitrile, enol ether or enol thioether containing at least one proton and is often electron-deficient such as acrylate ester or an acrylonitrile. (A. de Meijere and F. E. Meyer, *Angew. Chem. Int. Ed. English* 1994 33:2379-2411; W. Cabri and I. Candiani, *Acc. Chem. Res.* 1995 28(1):2-7). Commonly used palladium catalysts include Pd(PPh$_3$)$_4$, Pd(OAc)$_2$, PdCl$_2$, Pd$_2$(dba)$_3$. Phosphine ligands such as PPh$_3$, P(o-Tol)$_3$ and BINAP are commonly incorporated into the reaction mixture either as preformed palladium complexes or as free phosphines which can form complexes in situ. Bases such as TEA, 1,2,2,6,6-pentamethyl-piperidine, DBU, K$_2$CO$_3$, KOAc, Ag$_2$CO$_3$ and KO-tert-Bu are typically required. The reaction is commonly run in aprotic solvents, frequently DMF, DMSO, NMP or acrylonitrile; however less polar solvents and aqueous cosolvents can also be utilized. While there are several reaction variables, protocols have been identified and one skilled in the art can identify useful conditions without undue experimentation.

Acid-catalyzed cyclization of 32 afforded 34 which was subjected to a Suzuki cross coupling with 2-benzyloxy-pyridin-3-yl boronic acid to afford 36a and subsequently treated with NBS to afford the bromolactam 36b. Many variously substituted aryl and heteroaryl boronic acids are available, e.g. 3-methanesulfonylamino-benzene boronic acid, that can be introduced by a second Suzuki cross coupling with to afford 38a. Cleavage of the benzyl ether by catalytic hydrogenolysis or by acid catalyzed cleavage in the presence of HBr and HOAc affords the desire pyridone 39a (Ar=4-methanesulfonylamino phenyl). The ready availability of substituted boronic acids affords easy access to Ar substitution with the scope of the present invention.

The Suzuki reaction is a palladium-catalyzed coupling of a boronic acid with an aryl or vinyl halide or triflate. Typical catalysts include Pd(PPh$_3$)$_4$, PdCl$_2$(dppf), Pd(OAc)$_2$ and PdCl$_2$(PPh$_3$)$_2$. With PdCl$_2$(dppf), primary alkyl borane compounds can be coupled to aryl or vinyl halide or triflate without beta-elimination. The reaction can be carried out in a variety of organic solvents including toluene, THF, dioxane, DCE, DMF, DMSO, MeOH, EtOH and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction such as the particular palladium catalyst, the ligand, additives, solvent, temperature, numerous protocols have been identified. Highly active catalysts have been described (see, e.g., J. P. Wolfe et al., *J. Am. Chem. Soc.* 1999 121(41): 9550-9561 and A. F. Littke et al., *J. Am. Chem. Soc.* 2000 122(17):4020-4028). One skilled in the art will be able to identify a satisfactory protocol without undue experimentation.

N-alkylation of the amide is conveniently carried out by treating 38a with a strong base and an alkylating agent to afford 38b prior to unmasking the pyridone.

SCHEME B

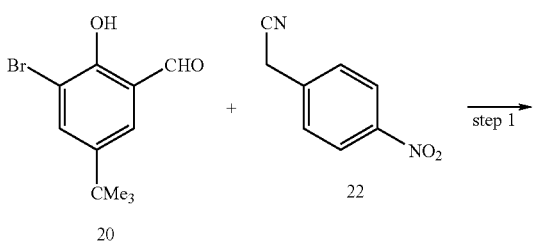

20      22

-continued

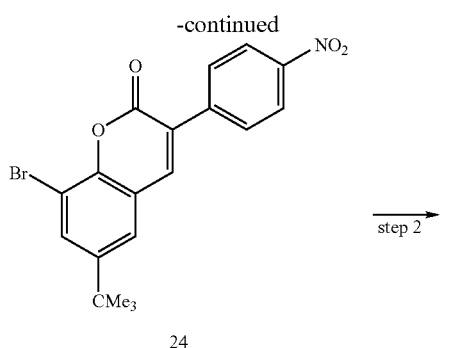

24

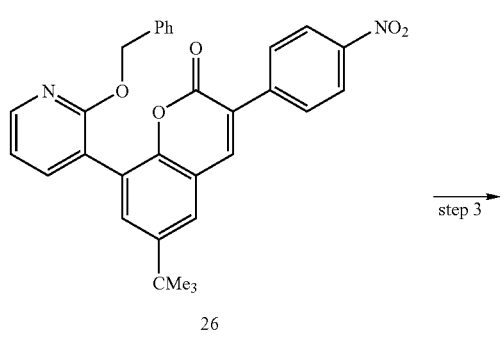

26

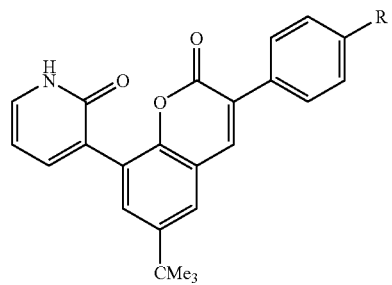

28a: R = NH₂
step 4
I-5: R = NHSO₂Me

Alternately, the three carbon fragment can be elaborated by introducing a two-carbon fragment onto a ortho-hydroxy or ortho-amino-benzaldehyde utilizing the Knoevenagel condensation. The Knoevenagel condensation is the condensation of aldehydes and ketones with carbon acids of the form Z—CH₂—Z' or Z—CHR—Z' wherein Z and Z' can be selected from among CHO, COR, CO₂H, CO₂R, CN, NO₂, SOR, SO₂R, and the like. Primary and secondary amine bases can be used to catalyze the reaction, alternatively pyridine containing a catalytic amount of piperidine is satisfactory. When Z' is hydrogen, the condensation can be carried out with strong base such as NaOEt, KO-tert-Bu, lithium di-isopropyl amide and the like. When Z' is aryl and Z is as defined above the condensation can be carried out with bases such as alkali or alkaline metal hydroxides or carbonates. The reaction is applicable to a wide range of carbon acids and the base is selected to be sufficiently basic to deprotonate the reactant. (Jones, *Org. Reactions* 1967 15:204-599)

The base-catalyzed condensation of 4-nitro-phenylacetonitrile and 20 in aqueous EtOH and subsequent hydrolysis of the nitrile affords the chromen-2-one 24. The masked pyridone is introduced by a Suzuki coupling as described above. Hydrogenation of 26 resulted in the concomitant reduction of the nitro group and hydrogenolysis of the benzyl ether to afford I-3. Sulfonylation of the resulting amine with a sulfonyl chloride affords the corresponding sulfonamide I-5 within the scope of the preset invention.

DIBAL reduction of 70b afforded the hemiacetal 72 which was directly converted to the pyridone by Suzuki coupling of 72 and B-(1,2-dihydro-2-oxo-3-pyridinyl)-boronic acid as described in Example 8.

SCHEME C

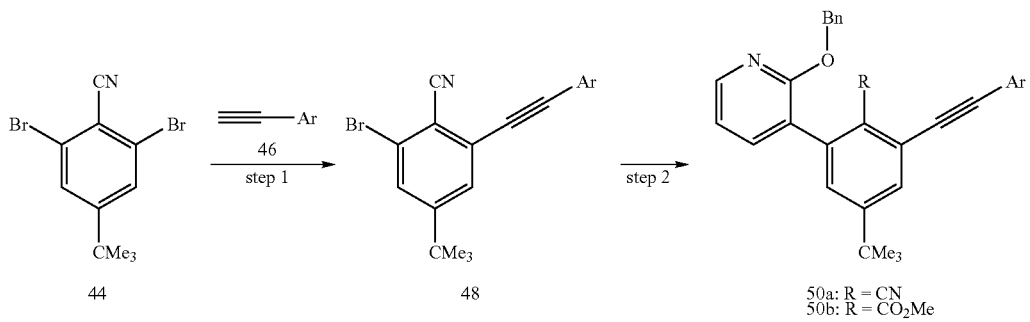

44     48     50a: R = CN
50b: R = CO₂Me

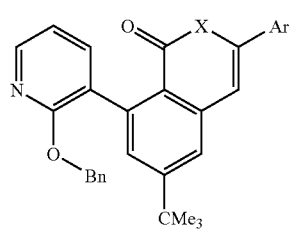 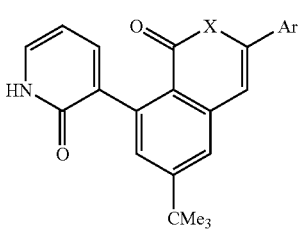 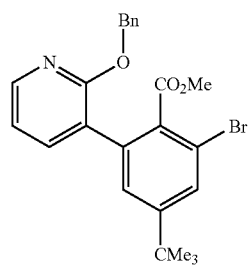

52a: X = NH
52b: X = O

I-14: X = NH
I-15: X = O

56

2H-Isoquinolin-1-ones and isochromen-1-ones can be prepared by introduction of a two-carbon fragment ortho to the carboxylic acid. In one approach an acetylene 46 is coupled to 4-tert-butyl-2,6-dibromo-benzonitrile (44) utilizing the Sonogashira-coupling protocol. The Sonogashira coupling (K. Sonogashira et al., *Tetrahedron Lett.* 1975 4467-4470; K. Sonogashira, *Comprehensive Organic Synthesis*; B. M. Trost and I. Fleming Eds.; Pergamon Press, Oxford, 1991; Vol. 3, Chapter 2.4, p 521) is typically carried out in the presence of a palladium catalyst such as $Pd(PPh_3)_4$ or $Pd(II)$ $Cl_2(PPh_3)_2$ and a cuprous salt such as CuI, a dialkyl- or trialkylamine such as diethylamine, diisopropylamine and TEA at temperature from RT to 100° C. The reaction can be carried out using the amine base as the solvent or with other organic solvents including hydrocarbons, ethers, alcohols, aqueous DMA and the like. The existence of alternative procedures affords flexibility in the synthetic planning permitting introduction of a variety of substituted aryl and heteroaryl substituents.

The masked pyridone is then introduced by a Suzuki coupling as described above to afford 50a. When the nitrile is hydrolyzed with hydrido(dimethylphosphinous acid-kP)[hydrogen bis(dimethylphosphnito-kP]platinum (II) (CASRN 173416-05-2; X-b Jiang et al., Platinum-Catalyzed Selective Hydration of Hindered Nitriles and Nitriles with Acid- or Base Sensitive Groups, *J. Org. Chem.* 2004 69(7):2327-31; T. Ghaffar and A. W. Parkins, A New Homogenous Platinum Containing Catalyst for the Hydrolysis of Nitriles. *Tetrahedron Lett.* 1995 36(47):8657-8660), an intramolecular cycloisomerization occurred to afford the desired 2H-isoquinolin-1-ones 52a occurred. Hydrogenolysis of the benzyloxypyridine unmasks the desired pyridone I-14.

Gold salts have been demonstrated to catalyze the cycloisomerization of acetylenic acids and esters (E. Genin et al., *J. Am. Chem. Soc.* 2006 128(10):3112-3113). Methyl 2-phenylethynyl-benzoates undergo $AuCl_3$-mediated 6-endo cyclization to afford the desires isochromen-1-ones 56b. (E. Marchal et al., *Tetrahedron* 2007 63:9979-9990) The requisite acetylenic ester was prepared by a Sonogashira coupling of 56 and an optionally substituted phenyl acetylene (step 5). The $AuCl_3$ catalyzed cyclization of 50b afforded 52b which was debenzylated to afford the pyridone as described previously to afford I-15.

In contrast to the $AuCl_3$-catalyzed endo cyclization, oxidation of N-{4-[3-(2-benzyloxy-pyridin-3-yl)-5-tert-butyl-2-formyl-phenylethynyl]-phenyl}-methanesulfonamide (66) occurred with concomitant exo-cyclization to afford 68. Depending upon the conditions employed for the hydrogenolysis of the benzyl ether the recovered compound was either I-16 or I-17 (Example 7)

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

N-{4-[6-tert-Butyl-2-oxo-8-(2-oxo-1,2-dihydro-pyridin-3-yl)-2H-chromen-3-yl]-phenyl}-methanesulfonamide (I-5)

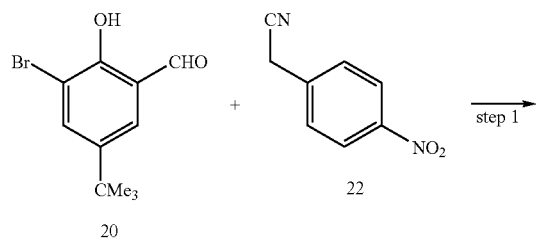

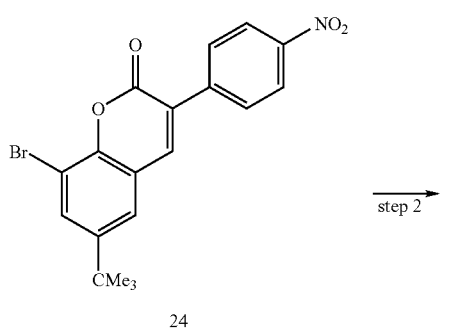

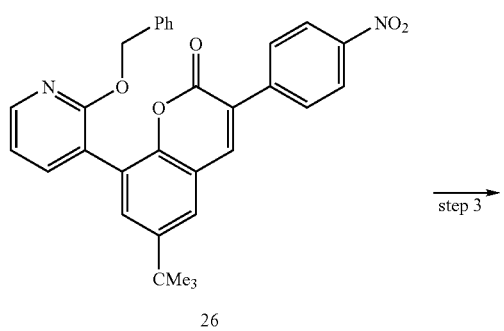

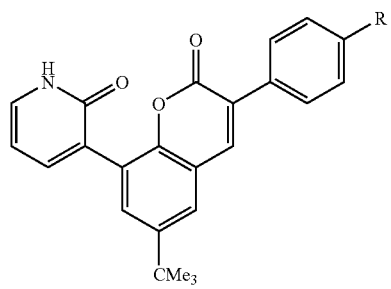

28a: R = NH$_2$
step 4 ⟶ I-5: R = NHSO$_2$Me 2-benzyloxy-pyridin-3-ylboronic acid (25)—A solution of 2-benzyloxy-3-bromo-pyridine (2.50 g, 9.47 mmol), Pd(II)Cl$_2$(PPh$_3$)$_2$ (232 mg, 0.28 mmol), KOAc (2.32 g, 23.67 mmol), bis-(pinacolato)diborane (2.95 g, 11.36 mmol) and DME (75 mL) was heated at 70° C. for 26 h. The reaction mixture was cooled and partitioned between Et$_2$O and water. The organic phase was separated, dried and evaporated. The crude product was purified by SiO$_2$ chromatography eluting with a EtOAc/hexane gradient (0 to 5% EtOAc) to afford 1.81 g of 25 containing a small amount of bis-(pinacolato)diborane.

step 1—A mixture of 20 (2.00 g, 7.78 mmol), 22 (1.06 g, 7.78 mmol), NaOH (0.078 g, 1.94 mmol), trimethyl cetyl ammonium bromide (0.28 g, 0.78 mmol), H$_2$O (50 mL) and EtOH (5 mL) was stirred at RT for 2 d. The reaction mixture was acidified with con HCl to a pH of ca. 2. The mixture was heated at 90° C. for 4 h then allowed to cool to RT. The light-brown precipitate was collected by filtration, washed with H$_2$O and dried in a vacuum oven at 50° C. to afford 1.12 g of 24.

step 2—A tube was charged with 24 (0.340 g, 0.845 mmol), 25 (0.252 g, 1.90 mmol), Pd(dppf)$_2$Cl$_2$·CH$_2$Cl$_2$ (0.034 g, 0.042 mmol), Na$_2$CO$_3$ (0.134 g, 1.268 mmol), MeOH (5 mL) and DCM (1 mL), sealed and irradiated in a microwave synthesizer at 115° C. for 30 min. The reaction mixture was concentrated in vacuo. The crude product was purified by SiO$_2$ chromatography eluting with an EtOAc/hexane gradient (5 to 25% EtOAc) to afford 0.256 of 26.

step 3—A mixture of 26 (0.129 g), Pd(OH)$_2$/C (0.040 g), EtOAc (15 mL) and MeOH (5 mL) was stirred for 2 h under 1 atm of hydrogen. The catalyst was filtered and the filtrated concentrated in vacuo. The crude product was purified on a preparative SiO$_2$ TLC plate developed with 1% MeOH/EtOAc to afford 36 mg of 28 along with 44 mg of slightly impure 28.

step 4—To a solution of 28 (0.100 g, 0.26 mmol) in DCM (5 mL) cooled to 0° C. was added sequentially pyridine (52 μL, 0.65 mmol) and mesyl chloride (24 μL, 0.31 mmol). The reaction was allowed to warm to RT and stirred overnight. The reaction mixture was diluted with EtOAc, washed sequentially with sat'd. aqueous CuSO$_4$, H$_2$O and brine, dried (MgSO$_4$), filtered and concentrated in vacuo. The crude product was purified on a preparative SiO$_2$ TLC plate developed with 20% EtOAc/hexane to afford 53 mg of I-5.

EXAMPLE 2

N-{3-[6-tert-Butyl-2-oxo-8-(2-oxo-1,2-dihydro-pyridin-3-yl)-1,2-dihydro-quinolin-3-yl]-phenyl}-methanesulfonamide (I-10)

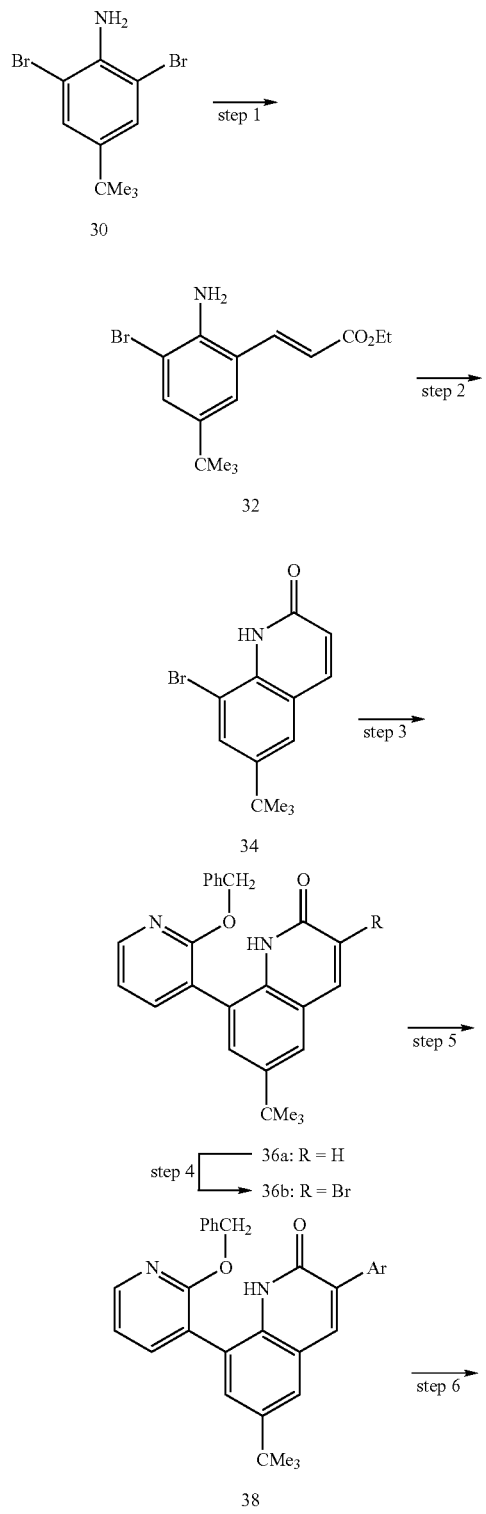

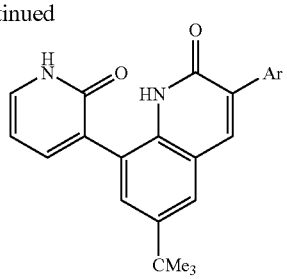

I-10
Ar = 3-methanesulfonylamino-phenyl step 1—To a solution of 30 (10.0 g) and MeCN (200 mL) was added tri-(o-tolyl)phosphine (1.33 g), Pd(II)(OAc)$_2$ (0.730 g), TEA (6.8 mL) and methyl acrylate (2.35 mL). The reaction was stirred overnight at 100° C. The reaction was cooled and concentrated in vacuo. The crude product was purified by SiO$_2$ chromatography eluting with an EtOAc/hexane gradient (0% EtOAc from 0-5 min, 20% EtOAc from 5.5-15 min and 40% EtOAc from 15.5-30 min) to afford 3.02 g of 32.

step 2—To a solution of 32 (6.73 g) and THF (150 mL) was added 6N HCl (150 mL) and the resulting solution was heated at 100° C. overnight. The solution was cooled and concentrated in vacuo. The reaction mixture was made basic with solid NaHCO$_3$ and thrice extracted with EtOAc (3×150 mL). The combined extracts were washed with brine, dried (Na$_2$SO$_4$), filtered and concentrated in vacuo. The crude product was purified by SiO$_2$ chromatography with the gradient described in step 1. The combined fractions were evaporated and triturated with Et$_2$O to afford 34 as an off white solid.

step 3—A microwave tube was charged with 34 (0.500 g), 25 (0.490 g), Pd(PPh$_3$)$_4$ (0.206 g), Na$_2$CO$_3$ (0.568 g), MeOH (9 mL) and DCM (3 mL), sealed and irradiated in a microwave synthesizer for 30 min at 115° C. The reaction was repeated four times and the combined reaction mixtures were concentrated and partitioned between H$_2$O and EtOAc (100 mL of each). The aqueous layer was twice extracted with EtOAc and the combined extracts were washed with brine, dried and concentrated in vacuo. The crude product was purified by SiO$_2$ chromatography eluting with an EtOAc/hexane gradient (20% EtOAc from 0-15 min, 40% EtOAc from 15.5-30 min and 60% EtOAc from 15-50 min) to afford 2.195 g of 36a.

step 4—To a solution of 36a (2.195 g) in DCM (100 mL) cooled to 0° C. was added NBS (2.03 g). The solution was allowed to warm to RT and stirred overnight. An additional aliquot of NBS (1.0 g) was added and stirring continued for another 24 h at RT then heated at 50° C. for 2 h. The reaction was cooled and concentrated in vacuo. The crude product was purified by SiO$_2$ chromatography eluting with an EtOAc/hexane gradient (0% EtOAc from 0-5 min, 20% EtOAc from 5.5-15 min and 40% EtOAc from 15.5-40 min) to afford 1.44 g of 36b.

step 5—A tube was charged with 36b (0.060 g), 3-methanesulfonylaminobenzene boronic acid (0.033 g), Pd(PPh$_3$)$_4$ (0.015 g), Na$_2$CO$_3$ (0.041 g), MeOH (3 mL) and DCM (1 mL), sealed and irradiated in a microwave synthesizer for 30 min at 115° C. The reaction was cooled the concentrated in vacuo. The crude product was purified by SiO$_2$ chromatography eluting with an EtOAc/hexane gradient (0% EtOAc from 0-5 min, 40% EtOAc from 5.5-15 min, 60% EtOAc from 15.5-30 min and 100% EtOAc from 30.5-40 min) to afford 0.042 g (59%) of 38.

step 6—To a suspension of 38 (0.040 g), EtOAc (10 mL) and MeOH (10 mL) was added Pd(OH)$_2$/C (catalytic quantity) and the reaction was stirred under a H$_2$ atmosphere (balloon) for 2 h, filtered and the filtrate concentrated. The crude product was purified on a SiO$_2$ preparative TLC plate developed first with 60% EtOAc (solvent run half wave up the plate, dried) and re-developed with 80% EtOAc/hexane and eluted to afford I-10.

The following were prepared analogously except in steps 3, 3-methanesulfonylamino-benzeneboronic acid was replaced with the boronic acid in parentheses: I-9 (4-methanesulfonylaminobenzeneboronic acid), I-6 (benzeneboronic acid), I-13 (B-[3-(aminocarbonyl)phenyl]-boronic acid) and I-11 (B-[4-(aminosulfonyl)phenyl]-boronic acid, CASRN 613660-87-0). I-2 can be prepared by hydrogenolysis of 36a.

EXAMPLE 3

N-{4-[6-tert-Butyl-1-methyl-2-oxo-8-(2-oxo-1,2-dihydro-pyridin-3-yl)-1,2-dihydro-quinolin-3-yl]-phenyl}-methanesulfonamide (I-8)

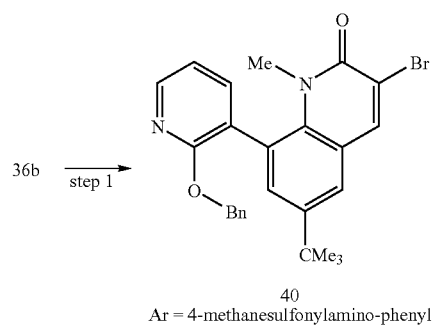

40
Ar = 4-methanesulfonylamino-phenyl

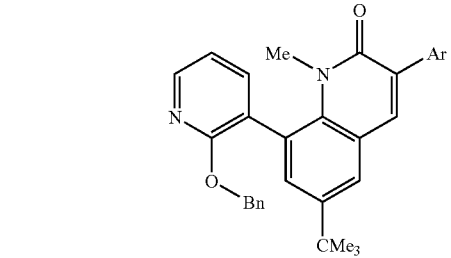

42 step 1—To a solution of 36b (0.500 g) in DMSO (5 mL) cooled to 0° C. was added NaH (0.049 g, 60% dispersion in mineral oil) followed by iodomethane (0.10 g). The ice-bath was removed and the reaction mixture was allowed to stir at RT for 30 min. The reaction mixture was partitioned between H$_2$O and EtOAc. The EtOAc layer was thrice extracted with H$_2$O (3×50 mL) and the combined aqueous extracts thrice back-extracted with EtOAc (3×50 mL). The combined EtOAc extracts were washed with brine, dried (Na$_2$SO$_4$), filtered and concentrated in vacuo. The crude product was purified by SiO$_2$ chromatography eluting with an EtOAc/hexane gradient (0% EtOAc from 0-5 min, 20% EtOAc from 5.5-15 min, 40% EtOAc from 15.5-25 min and 60% EtOAc from 25.5-35 min) to afford 40.

Suzuki coupling of 40 and 4-methanesulfonylaminobenzene boronic acid (step 2) and hydrogenolysis of the benzyl ester were carried out in accord with steps 5 and 6 of example 2 to afford I-8.

I-12 and I-7 were prepared analogously except in step 3, 4-methanesulfonylamino-benzeneboronic acid was replaced with B-[4-(aminosulfonyl)phenyl]-boronic acid (CASRN 613660-87-0) and 4-hydroxy-benzene boronic acid, respectively.

EXAMPLE 4

N-{4-[6-tert-Butyl-1-oxo-8-(2-oxo-1,2-dihydro-pyridin-3-yl)-1,2-dihydro-isoquinolin-3-yl]-phenyl}-methanesulfonamide (I-14)

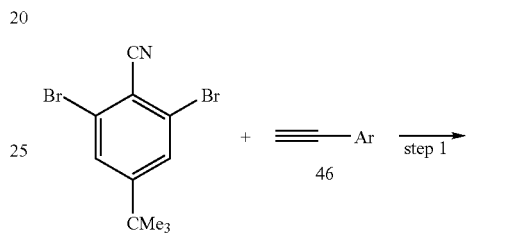

44

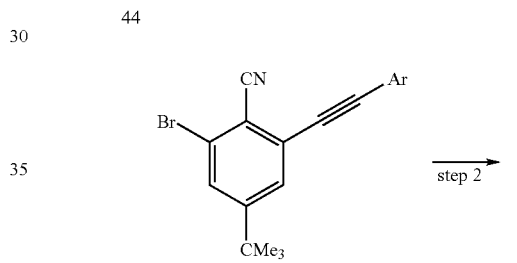

48

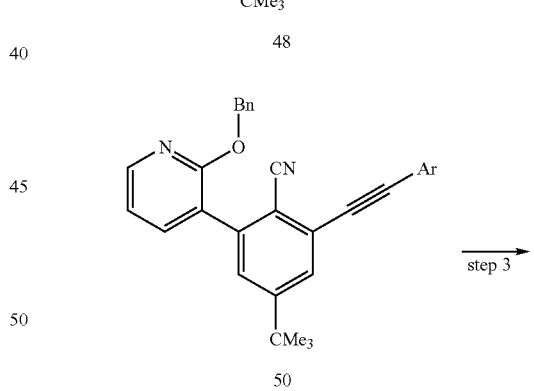

50

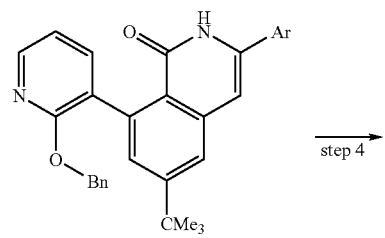

52
Ar = 4-methanesulfonylamino-phenyl

I-14 step 1—To a solution of 44 (0.750 g, 1.9 mmol, CASRN 80578-102) and 46 (0.748 g, CASRN 111448-81-8) in THF (15 mL) was added CuI (0.027 g), DIPEA (5 mL) and Pd(PPh$_3$)$_2$Cl$_2$ (0.023 g) and the reaction was heated at 80° C. overnight. The reaction was cooled to RT and concentrated in vacuo. The product was purified by SiO$_2$ chromatography eluting with an EtOAc/hexane gradient (0% EtOAc from 0-5 min, 20% EtOAc from 5.5-20 min and 40% EtOAc from 20.5-30 min) to afford 0.290 g (24%) of 48.

step 2—Suzuki coupling of 48 and 25 was carried out in accord with the procedure described in step 3 of example 2 to afford 50 which was purified by SiO$_2$ chromatography eluting with an EtOAc/hexane gradient (0% EtOAc from 0-5 min, 20% EtOAc from 5.5-15 min and 40% EtOAc from 15.5-25 min).

step 3—To a solution of 50 (0.113 g) and EtOH (5 mL) was added hydrido(dimethylphosphinous acid-kP)[hydrogen bis(dimethylphosphnito-kP]platinum (II) (Stem Chemicals Inc., 78-0725, CASRN 173416-05-2) and the resulting solution stirred at reflux overnight. The reaction was cooled to RT and concentrated. The residue was partitioned between EtOAc and H$_2$O (25 mL each). The aqueous layer was twice washed with EtOAc (2×25 mL). The EtOAc extracts were combined, washed with brine, dried (Na$_2$SO$_4$), filtered and concentrated. The crude product was purified on a preparative SiO$_2$ TLC plate developed with 10% MeOH/DCM to afford 0.106 g of 52.

step 4—Debenzylation of 52 was carried out in accord with the procedure described in step 3 of example 1. The product was purified on a preparative SiO$_2$ TLC plate developed with 10% MeOH/DCM. The eluted product was triturated with DCM containing a trace of MeOH and the resulting solid collected by filtration.

EXAMPLE 5

N-{4-[6-tert-Butyl-1-oxo-8-(2-oxo-1,2-dihydro-pyridin-3-yl)-1H-isochromen-3-yl]-phenyl}methanesulfonamide (I-15)

step 1
54a: R = NH$_2$
54b: R = CN step 3
56a: R = CN
step 4
56b: R = CHO
56c: R = CO$_2$H
step 5
56d: R = CO$_2$Me 58
Ar = 4-methylsulfonylamino-phenyl
Bn = benzyl

I-15     60 step 1—To a stirred mixture of 54a (13.08 g, 42.60 mmol, CASRN 10546-67-5) in water (16 mL) and HOAc (26 mL) was added concentrated sulfuric acid (11.20 mL, 119.28 mmol). The mixture was heated to completely dissolve the solids. The solution was cooled to 10° C. and an aqueous solution of sodium nitrite (3.08 g, 46.86 mmol) in water (30 mL) over a period of 10 min with vigorous stirring until the mixture became a light brown solution.

To a mixture of CuSO$_4$ (7.68 g, 51.12 mmol) in water (30 mL) and ice (40 g) was added KCN (13.00 g, 213.01 mmol) while maintaining the temperature below 20° C. by adding more ice. The precipitate that initially formed dissolved. Finally, NaHCO$_3$ (26.80 g, 340.81 mmol) and benzene (60 mL) were added to the mixture. The solution containing the diazonium salt (supra) was added dropwise to this solution at 50-55° C. over 30 min while stirring vigorously. The mixture was stirred for additional 30 min upon the completion of addition. The reaction mixture was cooled to RT then diluted with benzene (200 mL). The organic layer was washed with 2N NaOH solution, brine, dried (Na₂SO₄), filtered and concentrated. The residue was fractionally recrystallized from a mixture of DCM and ether to afford 7.84 g (58%) of 2,6-dibromo-4-tert-butyl-benzonitrile (54b) as a light brown solid.

step 2—Suzuki coupling of 54b and 25 was carried out in accord with the procedure described in step 3 of example 2 to afford 56a. The crude product was purified by SiO₂ chromatography eluting with a EtOAc/hexane gradient (15 to 25% EtOAc) to afford 1.0 g of 56a.

step 3—To a solution of 56a (1.0 g, 2.4 mmol) in toluene (20 mL) cooled to −75° C. was added dropwise a solution of DIBAL (2.9 mL of a 1M solution in DCM) and the resulting reaction mixture stirred at −75° C. for 3 h then poured into ice cold 5% aqueous H₂SO₄. The layers were separated and the aqueous layer was extracted with EtOAc. The toluene and EtOAc solutions were combined and washed with brine, dried (MgSO₄), filtered and evaporated. The crude product was purified by SiO₂ chromatography eluting with a EtOAc/hexane gradient (5 to 35% EtOAc) to afford 0.0 73 g (72%) of 56b.

step 4—To a solution of 56b (0.73 g, 1.72 mmol), Na₂HPO₄ (2.85 g, 20.6 mmol), 2-methyl-2-butene (3.7 mL, 34.4 mmol) in tert-BuOH (30 mL), H₂O (30 mL) and THF (10 mL) cooled to 5° C. was added NaClO₂ (0.39 g, 4.3 mmol). The reaction mixture was allowed to warm to RT and stirred for 7 h. Additional 2-methyl-2-butene (1.0 mL) and NaClO₂ (0.9 g) were added and reaction was stirred overnight then poured into a mixture of ice and 1N HCl. The solution was twice extracted with EtOAc and the combined extracts dried (Na₂SO₄), filtered and concentrated to afford 0.76 g (100%) of 56c.

step 5—To a solution of 56c (0.76 g, 1.72 mmol), MeOH (5 mL) and DCM (15 mL) cooled to 5° C. was added dropwise trimethylsilyl-diazomethane (1.29 mL, 2M solution in hexanes) over a 30 min period. The reaction was concentrated in vacuo. The crude product was purified by SiO₂ chromatography eluting with an EtOAc/hexane gradient (2 to 15% EtOAc) to afford 0.674 g (86%) of 56d as a white solid.

step 6—A flask was charged with 56d (0.49 g, 1.08 mmol), N-(4-ethynylphenyl)-methanesulfonamide (0.31 g, 0.156 mmol, CuI (0.021 g, 0.108 mmol) and DMF (8 mL). The solution was sparged with Ar for 5 min then Pd(PPh₃)₂Cl₂ (0.15 g, 0.2 mmol) was added and the solution stirred for 5 min before the addition of DIPEA (4 mL). The resulting reaction mixture was heated to 75° C. for 2 h then stirred overnight at RT. The solution was diluted with 1N HCl and extracted with EtOAc. The extracts were washed sequentially with water and brine, dried, filtered and evaporated to afford 0.163 g (27%) of 58.

step 7—To a solution of 58 (0.163 g, 0.29 mmol) dissolved in anhydrous MeCN (2 mL) was added H₂O (0.01 mL) and Ar gas bubbled through the solution for 3 min then AuCl₃ (0.009 g, 0.029 mmol) was added. Sparging with Ar was continued for another 3 min then the reaction was stirred at 50° C. under Ar for 3 d. Two addition quantities of AuCl₃ were added over that period to push the reaction to completion. The solution was cooled and filtered through CELITE and the pad washed with EtOAc. The filtrated was evaporated and the crude product purified on two preparative SiO₂ TLC plates developed with 10% EtOAc/DCM to afford 30 mg (19%) of I-15.

EXAMPLE 6

3-(6-tert-Butyl-2-oxo-2H-chromen-8-yl)-1H-pyridin-2-one (I-1)

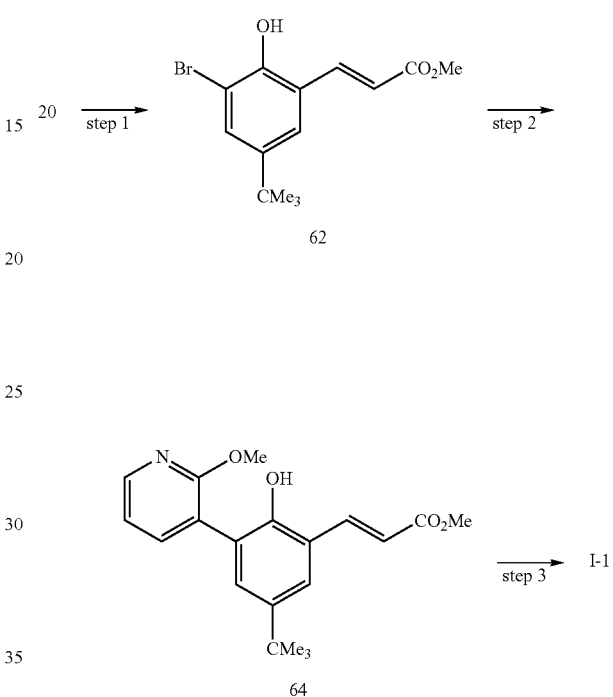

step 1—To a solution of methyl (dimethoxy-phosphoryl)-acetate (1.25 mL, 7.22 mmol) in THF (10 mL) cooled to 0° C. was added NaHMDS (16 mL, 1.0 M in THF). The solution was stirred for 15 min then a solution of 20 (1.0 g, 3.89 mmol) and THF (10 mL) was added. The solution was allowed to warm to RT and stirred overnight. The reaction was quenched with water and extracted with EtOAc. The extracts were dried (MgSO₄), filtered and evaporated. The crude product was purified by SiO₂ chromatography eluting with 5% EtOAc/hexane to afford 0.72 g of 62.

step 2—Suzuki condensation of 62 and B-(2-methoxy-3-pyridinyl)-boronic acid (CASRN 163105-90-6) was carried out in accord with the procedure described in step 3 of example 2 to afford 64 which was purified by SiO₂ chromatography eluting with an EtOAc/hexane gradient (0 to 15% EtOAc).

step 3—A solution of 64 (0.120 g), 48% HBr (125 μL) and HOAc (4 mL) in a sealed tube was heated at 70° C. overnight. The reaction mixture was cooled, diluted with EtOAc and poured in a 1 M NaHCO₃ solution. The organic phase was dried (MgSO₄), filtered and evaporated. The crude product was purified by SiO₂ chromatography eluting with an EtOAc/hexane gradient (50 to 75% EtOAc) to afford 0.028 g (25%) of I-1 along with the corresponding cinnamic acid.

EXAMPLE 7

N-{4-[6-tert-Butyl-3-oxo-4-(2-oxo-1,2-dihydro-pyridin-3-yl)-3H-isobenzofuran-(1Z)-ylidenemethyl]-phenyl}-methanesulfonamide (I-16) and N-{4-[6-tert-Butyl-3-oxo-4-(2-oxo-1,2-dihydro-pyridin-3-yl)-1,3-dihydro-isobenzofuran-1-ylmethyl]-phenyl}-methanesulfonamide (I-17)

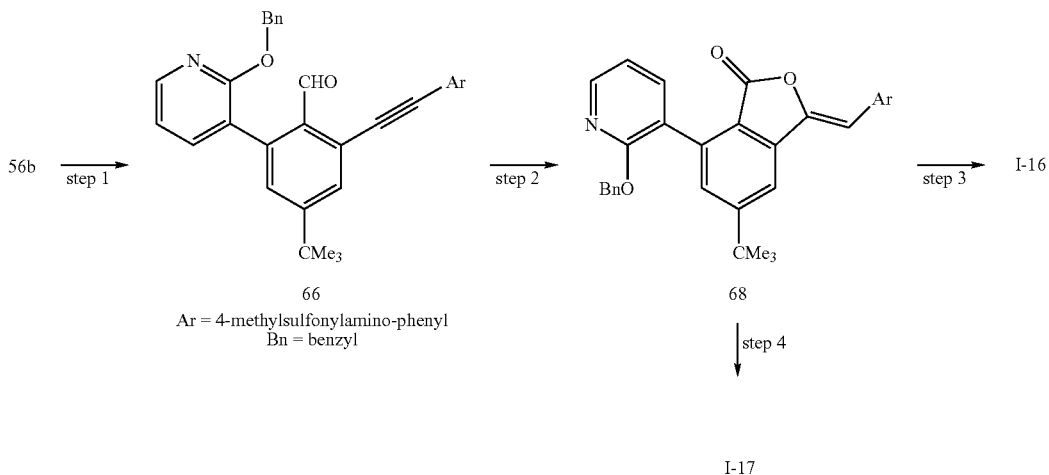

step 1—Condensation of 56b and N-(4-ethynylphenyl)-methanesulfonamide was carried out in accord with the procedure described in step 6 of example 5.

step 2—To a solution of 66 (0.186 g, 0.35 mmol), $Na_2HPO_4$ (0.58 g, 4.2 mmol), 2-methyl-2-butene (0.75 mL, 7 mmol) in tert-BuOH (9 mL), $H_2O$ (9 mL) and THF (3 mL) cooled to 5° C. was added $NaClO_2$ (0.08 g, 0.863 mmol). The reaction mixture was allowed to warm to RT and stirred for 7 h. Additional 2-methyl-2-butene (1.0 mL) and $NaClO_2$ (0.9 g) were added and reaction was stirred overnight then poured into 1N HCl. The solution was twice extracted with EtOAc and the combined extracts washed three times with water then with brine, dried, filtered and concentrated. The crude product was purified by $SiO_2$ chromatography eluting with an EtOAc/hexane gradient (20 to 80% EtOAc) to afford 0.168 g (87%) of 68 as a yellow film which solidified.

step 3—A suspension of 68 (0.050 g), 10% Pd/C (9.5 mg), EtOAc (25 mL) and MeOH (25 mL) was shaken in a Parr shaker for 2.5 h under 50 psi of hydrogen. The reaction mixture was filtered through CELITE and the pad washed with EtOAc. The filtrate was concentrated and purified with two sequential preparative $SiO_2$ plates developed with 5% MeOH/DCM to afford I-16.

step 4—Reduction of the olefin and hydrogenolysis of the benzyl ether was carried out similarly except the reaction was run for 4 h. The product was purified by preparative TLC on $SiO_2$ plates developed with 60% MeOH/DCM to afford 13.8 g of I-17.

EXAMPLE 8

N-{4-[6-tert-Butyl-2-hydroxy-8-(2-oxo-1,2-dihydro-pyridin-3-yl)-chroman-3-yl]-phenyl}-methanesulfonamide (I-18)

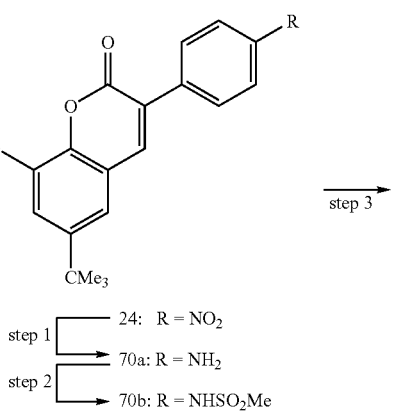

-continued

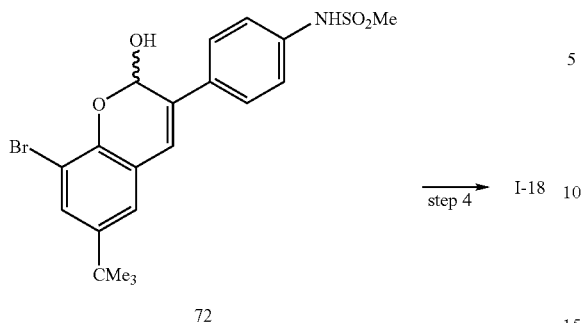

72 step 4 → I-18 step 1—To a suspension of 24 (0.967 g, 2.4 mmol) in MeOH (60 mL) and H₂O (30 mL) was added NH₄Cl (1.28 g, 24 mmol) and the mixture heated to between 65 and 70° C. Iron (0.67 g, 12 mmol) was added in portions over a 1 h period. After the addition was complete the reaction was stirred for an addition hour then cooled, filtered through CELITE and the filtrate evaporated. The residue was diluted with EtOAc, washed sequentially with H₂O and brine, dried, filtered and concentrated in vacuo to 0.906 g of 70a.

step 2—Conversion of 70a to the sulfonamide 70b with methanesulfonyl chloride was carried out in accord with the procedure described in step 4 of example 1.

step 3—To a solution of 70b (0.5 g, 1.1 mmol) dissolved in THF (20 mL) and cooled to −15° C. was added a solution of LiAlH₄ and THF (4.44 mL, 1.0 M solution in THF) and the resulting solution was stirred at RT overnight. The reaction mixture was carefully poured into 1N HCl and the resulting solution twice extracted with EtOAc. The combined extracts were washed with brine, dried, filtered and evaporated. The crude product was purified by SiO₂ chromatography eluting with an EtOAc/hexane gradient (20 to 85% EtOAc) to afford 72.

step 4—Suzuki-coupling of 72 and B-(1,2-dihydro-2-oxo-3-pyridinyl)-boronic acid (CASRN 951655-49-5) was carried out in accord with the procedure in step 3 of example 2 to afford I-18 which was purified on preparative SiO₂ plates developed with EtOAc.

EXAMPLE 9

N-{4-[3,3-Dimethyl-7-oxo-9-(2-oxo-1,2-dihydro-pyridin-3-yl)-2,3,7,8-tetrahydro-furo[3,2-g]quinolin-6-yl]-phenyl}-methanesulfonamide

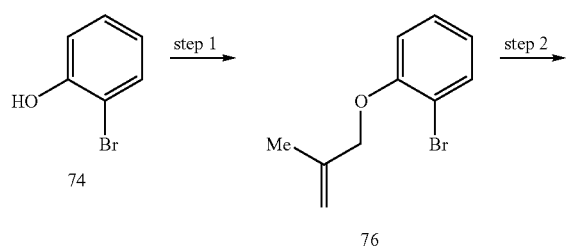

74  step 1 →  76  step 2 →

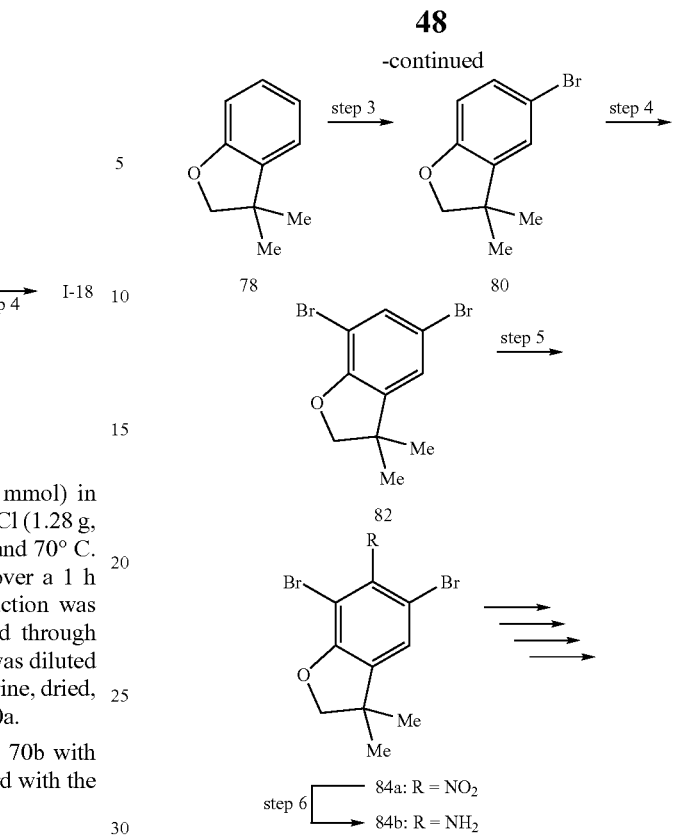

78 → step 3 → 80 → step 4 →

82

84a: R = NO₂
step 6
84b: R = NH₂

86 step 1—To a solution of 74 (2.457 g, 14 mmol) and acetone (75 mL) was added K₂CO₃ (4.907 g, 36 mmol) and 3-bromo-1-methyl propene (2.0 mL, 20 mmol) and the resulting solution was heated at reflux overnight. The reaction mixture was cooled and concentrated in vacuo. The residue was partitioned between EtOAc (150 mL) and H₂O (40 mL) The aqueous phase was extracted with EtOAc and the combined organic extracts were sequentially washed with H₂O and brine, dried (Na₂SO₄), filtered and concentrated in vacuo. The residue was purified by SiO₂ chromatography eluting with a EtOAc/hexane gradient (0 to 5% EtOAc) to afford 3.34 g (98.5%) of 76.

step 2—To a solution of 76 (3.33 g, 15 mmol) and benzene (150 mL) in a dried flask was added sequentially Bu₃SnH (6.625 g, 22 mmol) and AIBN (0.241 g) and the resulting solution heated at reflux overnight. The reaction mixture was cooled to RT, a 10% KF solution was added and the resulting two-phase mixture stirred vigorously for 2 h. The phases were separated and the organic phase was sequentially washed with sat'd aq. NaHCO₃ (50 mL) and brine. The combined organic extracts were dried (Na₂SO₄), filtered and evaporated. The crude product was purified by SiO₂ chromatography eluting with a DCM/hexane gradient (0 to 10% DCM to afford 1.855 g (85%) of 78.

step 3—To a solution of 78 (0.700 g, 5 mmol) and DMF (50 mL) in a dried flask was added NBS (1.765 g, 10 mmol) and the reaction was stirred overnight at RT. The reaction mixture was partitioned between H$_2$O (30 mL) and Et$_2$O (150 mL). The aqueous layer was separated and extracted with Et$_2$O (150 mL). The organic extracts were thrice washed with H$_2$O than once with brine. The combined organic extracts were dried (Na$_2$SO$_4$), filtered and concentrated in vacuo. The residue was adsorbed on SiO$_2$, added to the top of a SiO$_2$ column and eluted with hexanes to afford 0.9260 (90%) of 80.

step 4—To a solution of 80 (0.956 g, 4 mmol) and HOAc (8.0 mL) cooled to 0° C. was added a dropwise solution of Br$_2$ (320 µL, 6 mmol) and HOAc (2 ML) over a 10 min period. The reaction mixture was stirred overnight at RT. The reaction was quenched by addition of 10% Na$_2$S$_2$O$_3$ (10 mL) then HOAc was removed in vacuo. The residue was partitioned between Et$_2$O (100 mL) and sat'd. aq. NaHCO$_3$ (20 mL). The aqueous layer was separated and extracted with Et$_2$O (100 mL). The organic extracts were washed twice with sat'd. NaHCO$_3$ (20 mL) and once with H$_2$O. The combined extracts were dried (Na$_2$SO$_4$), filtered and evaporated. The residue was adsorbed on SiO$_2$, added to the top of a SiO$_2$ column and eluted with hexanes to afford 1.22 (95%) of 82.

step 5—The dihydrofuran 82 is treated with concentrated H$_2$SO$_4$ (2 mL) with stirring and is cooled to 0° C. HNO$_3$ (69%) is added dropwise and the reaction mixture is stirred at 0° C. for 10 min. The reaction mixture is partitioned between water and Et$_2$O, and the organic layer is concentrated. The crude material can be purified by SiO$_2$ chromatography eluting with hexane or an EtOAc/hexane gradient to afford 84a.

step 6—To a solution of 84a and EtOAc (30 mL) is added tin chloride dihydrate. The reaction mixture is stirred overnight at RT and then is partitioned between EtOAc and saturated NaHCO$_3$ and filtered through CELITE. The organic layer is separated, washed with water, dried (Na$_2$SO$_4$), filtered and evaporated. The crude product is purified by SiO$_2$ chromatography eluting with a EtOAc/hexane gradient to afford 84b.

The aniline 84b can be converted to the title compound by adapting the procedures described in steps 1 to 6 of example 2.

EXAMPLE 10

N-{4-[5-Methoxy-6-(1-methyl-cyclopropyl)-2-oxo-8-(2-oxo-1,2-dihydro-pyridin-3-yl)-1,2-dihydro-quinolin-3-yl]-phenyl}-methanesulfonamide (98)

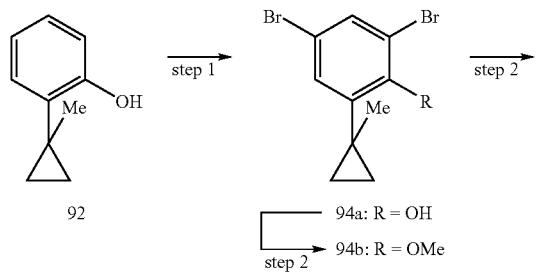

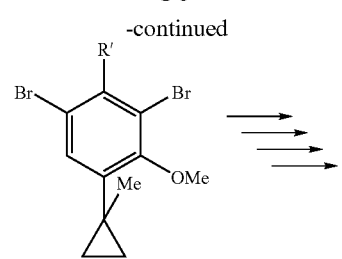

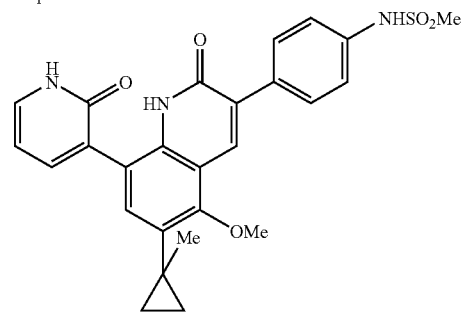

step 1: To a solution 92 in DCM-MeOH was added tetrabutylammonium tribromide (2.0 equivalents) and the resulting mixture is stirred at RT. The solvent is removed under reduced pressure and the residue is partitioned between EtOAc and water. The EtOAc layer is washed sequentially with water and brine, dried (Na$_2$SO$_4$), filtered and concentrated. The crude residue can purified by SiO$_2$ chromatography eluting with an EtOAc/hexane gradient to afford 94a.

step 2—To a solution of 94a (0.44 g, 1.7 mmol) in DMF is added K$_2$CO$_3$ (2.5 equivalents) and iodomethane (1.3 equivalents). The resulting mixture is stirred at 60° C. The reaction mixture is cooled to RT and partitioned between water and Et$_2$O. The organic layer is washed sequentially with water and brine, dried (Na$_2$SO$_4$), filtered and concentrated to afford 94b.

step 3—The dibromide 94b is treated with concentrated H$_2$SO$_4$ (2 mL) with stirring and is cooled to 0° C. HNO$_3$ (69%) is added dropwise and the reaction mixture is stirred at 0° C. for 10 min. The reaction mixture is partitioned between water and Et$_2$O, and the organic layer is concentrated. The crude material can be purified by SiO$_2$ chromatography eluting with hexane or an EtOAc/hexane gradient to afford 96a.

step 4—To a solution of 96a and EtOAc is added tin chloride dihydrate. The reaction mixture is stirred overnight at RT and then is partitioned between EtOAc and saturated NaHCO$_3$ and filtered through CELITE. The organic layer is separated, washed with water, dried (Na$_2$SO$_4$), filtered and evaporated. The crude product is purified by SiO$_2$ chromatography to afford 96b.

The aniline 96b can be converted to the title compound by adapting the procedures described in steps 1 to 6 of example 2.

An analogous sequence starting from 2-tert-butyl-phenol will afford N-{-4-[6-tert-butyl-5-methoxy-2-oxo-8-(2-oxo-1,2-dihydro-pyridin-3-yl)-1,2-dihydro-quinolin-3-yl]-phenyl}-methanesulfonamide.

EXAMPLE 11

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radio labeled substrate was removed by filtration and scintillant was added to the washed and dried filter plate containing radio labeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µl enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from 7.5×10-5 M to 20.6×10-6 M), 1 µM each ATP, CTP, and GTP, 40 mM Tris-HCl pH 8.0, 40 mM NaCl, 4 mM DTT (dithiothreitol), 4 mM MgCl2, and 5 µl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting $$Y = \% \text{ Min} + \frac{(\% \text{ Max} - \% \text{ Min})}{\left[1 + \frac{X}{(IC_{50})^S}\right]} \quad (i)$$

equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

EXAMPLE 12

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 (1 of phosphate buffered saline (pH 7.0) (PBS) per well and lysed with 20 (1 of 1×*R. luciferase* Assay lysis buffer prior to incubation at room temperature for 20 min. The plate was then inserted into the Centro LB 960 microplate luminometer (Berthold Technologies), and 100 (1 of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity $IC_{50}$ (µM) | Cytotoxic Activity $CC_{50}$ (µM) |
|---|---|---|
| I-5 | 0.01 | 95.1 |

EXAMPLE 13

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |

| Composition for Oral Administration (C) | |
|---|---|
| Ingredient | % wt./wt. |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I:

$$A-R \qquad (I)$$

wherein:

A is 2 oxo-1,2-dihydro-pyridin-3-yl;

R is Ia, Ib or Ic;

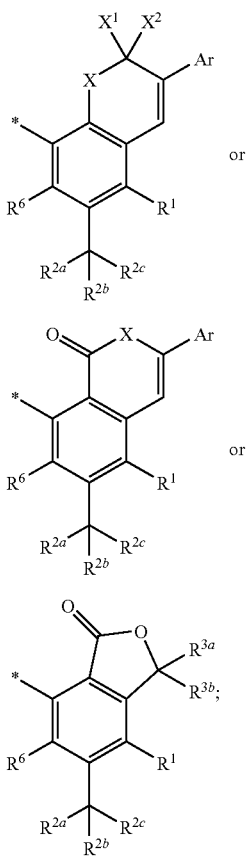

X is NR⁴ or O;

X¹ and X² together are oxo;

$R^{3a}$ is hydrogen and $R^{3b}$ is CH₂Ar or $R^{3a}$ and $R^{3b}$ together are =CHAr;

Ar is phenyl optionally independently substituted with one to three substitutents selected from the group consisting of (a) hydroxy, (b) $C_{1-6}$ alkoxy, (c) $C_{1-6}$ alkyl, (d) $C_{1-6}$ hydroxyalkyl, (f) halogen, (h) cyano, (i) $CO_2R^5$, (j) $CONR^cR^d$, (k) $C_{1-3}$ acylamino, (l) $(CH_2)_nNR^aR^b$, (m) $(CH_2)_nCONR^cR^d$, (n) $(CH_2)_nSO_2NR^cR^d$, (o) $(CH_2)_nSO_2R^5$ and (p) $O(CH_2)_nCONR^cR^d$;

$R^a$ and $R^b$ are independently in each occurrence (a) hydrogen, (b) $C_{1-6}$ alkyl, (c) $C_{1-6}$ acyl, (d) $C_{1-6}$ alkylsulfonyl, (e) $C_{1-6}$ haloalkylsulfonyl, (f) $C_{3-7}$ cycloalkylsulfonyl, (g) $C_{3-7}$ cycloalkyl-$C_{1-3}$ alkyl-sulfonyl or (h) $C_{1-6}$ alkoxy-$C_{1-6}$ alkylsulfonyl, (i) $SO_2(CH_2)_nNR^cR^d$, (j) carbamoyl, (k) $C_{1-3}$ alkylcarbamoyl, (l) $C_{1-3}$ dialkylcarbamoyl or (m) benzoyl said benzoyl optionally independently substituted with one or two groups selected from the group consisting of amino, halogen, $C_{1-6}$ alkyl or $C_{1-3}$ alkylsulfonylamino;

$R^c$ and $R^d$ are independently in each occurrence hydrogen, $C_{1-6}$ alkyl, $C_{1-6}$ acyl, or together with the nitrogen to which they are attached form a cyclic amine;

R¹ is hydrogen, $C_{1-6}$ alkyloxy or $C_{1-6}$ haloalkyloxy or R¹ and $R^{2a}$ together are CH₂—O and together with atoms to which they are attached form a 2,3-dihydrobenzofuran;

R⁶ is hydrogen;

R⁴ is hydrogen or $C_{1-6}$ alkyl;

R⁵ is hydrogen, $C_{1-6}$ alkyl, $C_{1-6}$ haloalkyl, $C_{1-3}$ alkoxy-$C_{1-3}$ alkyl or optionally substituted benzyl;

$R^{2a}$, $R^{2b}$ and $R^{2c}$ each are independently $C_{1-3}$ alkyl;

n is independently in each occurrence an integer from zero to three; or, a pharmaceutically acceptable salt thereof.

2. The compound according to claim 1 wherein R is Ia and $R^{2a}$, $R^{2b}$ and $R^{2c}$ each are methyl.

3. The compound according to claim 2 wherein Ar is phenyl substituted at least by $(CH_2)_nNR^aR^b$ wherein $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen and n is zero.

4. The compound according to claim 3 wherein $R^a$ is $C_{1-6}$ alkylsulfonyl.

5. The compound according to claim 1 wherein R is Ib.

6. The compound according to claim 5 wherein $R^{2a}$, $R^{2b}$ and $R^{2c}$ each are methyl.

7. The compound according to claim 6 wherein Ar is phenyl substituted at least by $(CH_2)_nNR^aR^b$, $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen and n is zero.

8. The compound according to claim 1 wherein R is Ic.

9. The compound according to claim 8 wherein $R^{3a}$ is hydrogen and $R^{3b}$ is CH₂Ar, Ar is optionally substituted phenyl and $R^{2a}$, $R^{2b}$ and $R^{2c}$ each are methyl.

10. The compound according to claim 9 wherein Ar is phenyl substituted at least by $(CH_2)_nNR^aR^b$, $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen and n is zero.

11. The compound according to claim 8 wherein $R^{3a}$ and $R^{3b}$ together are =CHAr, Ar is optionally substituted phenyl and $R^{2a}$, $R^{2b}$ and $R^{2c}$ are methyl.

12. The compound according to claim 11 wherein Ar is phenyl substituted at least by $(CH_2)_nNR^aR^b$, $R^a$ is $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, $R^b$ is hydrogen and n is zero.

13. The compound according to claim 1 selected from the group consisting of:

3-[3-(4-amino-phenyl)-6-tert-butyl-2-oxo-2H-chromen-8-yl]-1H-pyridin-2-one;

6-tert-butyl-8-(2-oxo-1,2-dihydro-pyridin-3-yl)-3-phenyl-1H-quinolin-2-one;

N-{4-[6-tert-butyl-2-oxo-8-(2-oxo-1,2-dihydro-pyridin-3-yl)-2H-chromen-3-yl]-phenyl}-methanesulfonamide;

6-tert-butyl-1-methyl-8-(2-oxo-1,2-dihydro-pyridin-3-yl)-3-phenyl-1H-quinolin-2-one;

6-tert-butyl-3-(4-hydroxy-phenyl)-1-methyl-8-(2-oxo-1,2-dihydro-pyridin-3-yl)-1H-quinolin-2-one;

N-{4-[6-tert-butyl-1-methyl-2-oxo-8-(2-oxo-1,2-dihydro-pyridin-3-yl)-1,2-dihydro-quinolin-3-yl]-phenyl}-methanesulfonamide;

N-{4-[6-tert-butyl-2-oxo-8-(2-oxo-1,2-dihydro-pyridin-3-yl)-1,2-dihydro-quinolin-3-yl]-phenyl}-methanesulfonamide;

N-{3-[6-tert-butyl-2-oxo-8-(2-oxo-1,2-dihydro-pyridin-3-yl)-1,2-dihydro-quinolin-3-yl]-phenyl}-methanesulfonamide;

4-[6-tert-butyl-2-oxo-8-(2-oxo-1,2-dihydro-pyridin-3-yl)-1,2-dihydro-quinolin-3-yl]-benzenesulfonamide;

4-[6-tert-butyl-1-methyl-2-oxo-8-(2-oxo-1,2-dihydro-pyridin-3-yl)-1,2-dihydro-quinolin-3-yl]-benzenesulfonamide;

3-[6-tert-butyl-2-oxo-8-(2-oxo-1,2-dihydro-pyridin-3-yl)-1,2-dihydro-quinolin-3-yl]-benzamide;

N-{4-[6-tert-butyl-1-oxo-8-(2-oxo-1,2-dihydro-pyridin-3-yl)-1,2-dihydro-isoquinolin-3-yl]-phenyl}-methanesulfonamide;

N-{-4-[6-tert-butyl-1-oxo-8-(2-oxo-1,2-dihydro-pyridin-3-yl)-1H-isochromen-3-yl]-phenyl}-methane sulfonamide;

N-{-4-[6-tert-Butyl-2-hydroxy-8-(2-oxo-1,2-dihydro-pyridin-3-yl)-chroman-3-yl]-phenyl}-methanesulfonamide;

N-{4-[6-tert-Butyl-3-oxo-4-(2-oxo-1,2-dihydro-pyridin-3-yl)-3H-isobenzofuran-(1Z)-ylidenemethyl]-phenyl}-methanesulfonamide; and, N-{-4-[6-tert-Butyl-3-oxo-4-(2-oxo-1,2-dihydro-pyridin-3-yl)-1,3-dihydro-isobenzofuran-1-ylmethyl]-phenyl}-methanesulfonamide; or, a pharmaceutically acceptable salt thereof.

14. A composition comprising a compound according to claim 1 admixed with at least one pharmaceutically acceptable carrier, diluent or excipient.

* * * * *